(12) United States Patent
Patterson (10) Patent No.: US 9,012,156 B2
(45) Date of Patent: *Apr. 21, 2015

(54) METHOD FOR THE SELECTION OF SPECIFIC AFFINITY BINDERS BY HOMOGENEOUS NONCOMPETITIVE ASSAY

(71) Applicant: Dynamic Affinity Reagents, LLC, Stoughton, WI (US)

(72) Inventor: William Patterson, Stoughton, WI (US)

(73) Assignee: Dynamic Affinity Reagents, LLC, Stoughton, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/012,720

(22) Filed: Aug. 28, 2013

(65) Prior Publication Data

US 2013/0345090 A1    Dec. 26, 2013

Related U.S. Application Data

(63) Continuation of application No. 12/888,188, filed on Sep. 22, 2010, now Pat. No. 8,524,457.

(60) Provisional application No. 61/244,770, filed on Sep. 22, 2009.

(51) Int. Cl.
  *G01N 33/53* (2006.01)
  *G01N 21/64* (2006.01)

(52) U.S. Cl.
  CPC ............ *G01N 21/6486* (2013.01); *G01N 33/53* (2013.01); *G01N 2500/04* (2013.01)

(58) Field of Classification Search
  None
  See application file for complete search history.

(56) References Cited

U.S. PATENT DOCUMENTS

| | | | |
|---|---|---|---|
| 4,458,066 | A  | 7/1984 | Caruthers et al. |
| 7,666,606 | B2 | 2/2010 | Waldo et al. |
| 7,935,493 | B2 | 5/2011 | Michnick et al. |
| 8,241,860 | B2 | 8/2012 | Ghosh et al. |
| 2006/0099646 | A1 | 5/2006 | Heding |
| 2007/0150970 | A1 | 6/2007 | Zuker |

FOREIGN PATENT DOCUMENTS

| | | |
|---|---|---|
| WO | 93/06868 | 4/1993 |
| WO | 94/08629 | 4/1994 |
| WO | 94/09056 | 4/1994 |

OTHER PUBLICATIONS

Thie, et al. "Phage Display Derived Therapeutic Antibodies" Curr. Pharm. Biotechnol. (2008) 9(6), 439-46.
Thøgersen, et al. "Intravenous immunoglobulin administration to a patient with systemic lupus erythematosus and pneumococcal septicemia" Innovations in Pharmaceutical Technology: Drug Discovery (2006) vol. February, p. 27-31.
Tomalia, et al. "Starburst Dendrimers: Molecular-Level Control of Size, Shape, Surface Chemistry, Topology and Flexibility from Atoms to•Macroscopic Matter" Angew. Chem. Int. Ed. Engl. 29:138-175 (1990).
Ullman, et al. "Luminescent oxygen channeling immunoassay: measurement of particle binding kinetics by chemiluminescence" (1994) Proc. Natl. Acad. Sci. USA 91(12), 5426-30.
Valanne, et al. "A novel homogeneous assay format utilising proximity dependent fluorescence energy transfer between particulate labels" (2005) Anal. Chim. Acta 539, 251-6.
Xu, et al. "A bioluminescence resonance energy transfer (BRET) system: Application to interacting circadian clock proteins" (1999) Proc. Natl. Acad. Sci. USA 96(1), 151-6.
Yao, et al. "A Bioluminogenic Substrate for In Vivo Imaging of β-Lactamase Activity" Angew. Chem. Int. Ed. (2007) 46, 7031-4.
Yu "Coiled-coils: stability, specificity, and drug delivery potential" Adv. Drug Deliv. Rev. (2002) 54(8), 1113-29.
Fellouse et al., "Molecular Recognition by a Binary Code." J. Mol. Biol. 2005, 348:1153-1162.
Renberg, "Fluorescence-based ligand assays for protein detection using affibody affinity proteins." Ph.D Dissertation 2006, Royal Institute of Technology (KTH), Department of Biotechnology, Stockholm Sweden, 90 pages.
"A Practical Guide to working with Alphascreen" Publication 2006, PerkinElmer Life and Analytical Sciences, 58 pages.
Arai "Detection of protein-protein interaction by bioluminescence resonance energy transfer from firefly luciferase to red fluorescent protein" J. Biosci. Bioeng. (2002) 94(4), 362-364.
Bailon, et al. "PEG-modified biopharmaceuticals" Expert Opin. Drug Deliv. (2009) 6(1), 1-16.
Baret et al. "Fluorescence-activated droplet sorting (FADS): efficient microfluidic cell sorting based on enzymatic activity" Lab Chip (2009) 9, 1850-1858.
Beaucage et al. "Deoxynucleoside Phosphoramidites—A New Class of Key Intermediates for Deoxypolynucleotide Synthesis" (1981) Tetrahedron Lett. 22:1859-1862.
Bertschinger, et al. "Covalent DNA display as a novel tool for directed evolution of proteins in vitro" Protein Eng. Des. Sel. 17(9), 699-707 (2004).
Binz, et al. "Engineering novel binding proteins from nonimmunoglobulin domains" Nat. Biotech. (2005) 23(10), 1257-68.
Brouzes et al. "Droplet microfluidic technology for single-cell high-throughput screening" PNAS (2009) early editionProc. Natl. Acad. Sci. USA 106(34), 14195-14195-14200.
Ciruela "Fluorescence-based methods in the study of protein-protein interactions in living cells" Curr. Opin. Biotechnol. (2008) 19(4), 338-43.

(Continued)

*Primary Examiner* — Jacob Cheu
(74) *Attorney, Agent, or Firm* — David A. Casimir; Casimir Jones, S.C.

(57) ABSTRACT

The invention generally relates to the field of immunochemistry including antibody therapy, diagnostics, and basic research and specifically relates to the area of selecting affinity molecules such as natural antibodies, including artificial antibodies, antibody mimics, and aptamers. The invention relates particularly to a method of selecting affinity molecules using a homogeneous noncompetitive assay in a high throughput process.

20 Claims, 2 Drawing Sheets

(56) References Cited

OTHER PUBLICATIONS

Daugherty "Protein engineering with bacterial display" Curr. Opin. Stud. Biol. (2007) 17(4), 474-80.

Dittrich, et al. "A new embedded process for compartmentalized cell-free protein expression and on-line detection in microfluidic devices" Chembiochem. (2005) 6(5):811-4.

Gai, et al. "Yeast surface display for protein engineering and characterization" Curr. Opin. Struct. Biol. (2007) 17(4), 467-73.

Ghadessy, et al. "A novel emulsion mixture for in vitro compartmentalization of transcription and translation in the rabbit reticulocyte system" Prot. Eng. Des. Sel. (2004) 17 (3), 201-4.

Gilbreth, et al. "A dominant conformational role for amino acid diversity in minimalist protein-protein interfaces" J. Mol. Biol. (2008) 381, 407-18.

Gullberg, et al. "Cytokine detection by antibody-based proximity ligation" (2004) Proc Natl Acad Sci U S A 101(22), 8420-8424.

Gullberg, et al. A sense of closeness: protein detection by proximity ligation Curr. Opin. Biotechnol. (2003) 14(1), 82-6.

Hanes, "Ribosome display efficiently selects and evolves high-affinity antibodies in vitro from immune libraries" (1998) Proc Natl Acad Sci U S A 95(24), 14130-5.

He, et al. "Ribosome display: next-generation display technologies for production of antibodies in vitro" F. Expert Rev. Proteomics (2005) 2(3), 421-30.

Hogbom, et al. "Structural basis for recognition by an in vitro evolved affibody" Proc. Nat. Acad. Sci. (2003) 100(6), 3191-6.

Hoogenboom "Selecting and screening recombinant antibody libraries" (2005) Nature Biotech 23(9), 1105-16.

Koch, et al. "Direct selection of antibodies from complex libraries with the protein fragment complementation assay" J. Mol. Biol. (2006) 357, 427-441.

Köhler, et al. "Continuous cultures of fused cells secreting antibody of predefined specificity" Nature (1975) 256 (5517):495-7.

Koide, et al. The fibronectin type III domain as a scaffold for novel binding proteins J. Mol. Biol. (1998) 284 (4):1141-51.

Koide, et al. "High-affinity single-domain binding proteins with a binary-code interface" Proc. Nat. Acad. Sci. (2007) 104(16), 6632-6637.

Kolmar "Alternative binding proteins: biological activity and therapeutic potential of cystine-knot miniproteins" FEBS J. (2008) 275(11), 2684-90.

Lamla, et al. "The Nano-tag, a streptavidin-binding peptide for the purification and detection of recombinant proteins" Protein Expr. Purif. (2004) 33(1), 39-47.

Liu, et al. "Optimized synthesis of RNA-protein fusions for in vitro protein selection" Meth. Enzymol. (2000) 318, 268-93.

Liu, et al. "A one-step homogeneous immunoassay for cancer biomarker detection using gold nanoparticle probes coupled with dynamic light scattering" (2008) J. Am. Chem. Soc. 130 (9), 2780-2.

Michnick, et al. "Universal strategies in research and drug discovery based on protein-fragment complementation assays" Nature Rev. (2007) 6, 569-82.

Michnick "Exploring protein interactions by interaction-induced folding of proteins from complementary peptide fragments" Curr. Opin. Struct. Biol. (2001) 11(4), 472-7.

Mössner, et al. "Fast selection of antibodies without antigen purification: adaptation of the protein fragment complementation assay to select antigen-antibody pairs" J. Mol. Biol. (2001) 308(2), 115-122.

Nuttall, et al. "Display scaffolds: protein engineering for novel therapeutics" Curr. Opin. Pharmacol. (2008) 8(5), 609-15.

Nuttall, et al. "Design and expression of soluble CTLA-4 variable domain as a scaffold for the display of functional polypeptides" Proteins (1999) 36, 217-27.

Ohiro, et al. "Enhanced fluorescence resonance energy transfer immunoassay with improved sensitivity based on the Fab'-based immunoconjugates" Anal. Biochem. (2007) 360, 266-272.

Paulmurugan, et al. "Monitoring protein-protein interactions using split synthetic renilla luciferase protein-fragment-assisted complementation" Anal. Chem. (2003) 75(7), 1584-9.

Pelletier, et al. "Oligomerization domain-directed reassembly of active dihydrofolate reductase from rationally designed fragments" (1998) Proc. Natl. Acad. Sci. USA, vol. 95, pp. 12141-6.

Porcheddu, et al. "Peptide nucleic acids (PNAs), a chemical overview" Curr. Med. Chem. (2005) 12(22), 2561-99.

Remy, et al. "Clonal selection and in vivo quantitation of protein interactions with protein-fragment complementation assays" Proc. Natl. Acad. Sci. USA (1999) 96, 5394-9.

Roberts, et al. "RNA-peptide fusions for the in vitro selection of peptides and proteins" (1997) PNAS 94(23), 12297-302.

Roovers, et al. "Nanobodies in therapeutic applications" Curr. Opin. Mol. Ther. (2007) 9(4), 327-35.

Rothe, et al. "In vitro display technologies reveal novel biopharmaceutics" The FASEB J. (2006) 20, 1599-1610.

Secco, et al. "Antibody library selection by the {beta}-lactamase protein fragment complementation assay" (2009) Prot. Evol. Des. Sel. 22(5), 149-158.

Sergeeva, et al. "Display technologies: application for the discovery of drug and gene delivery agents" Adv. Drug Deliv. Rev. (2006) 58(15), 1622-1654.

Shimizu, et al. "Cell-free translation reconstituted with purified components" Nature Biotechnology (2001) 19, 751-5.

Sidhu, et al. "Phage display for engineering and analyzing protein interaction interfaces" Curr. Opin. Struct. Biol. (2007) 17(4), 481-7.

Silverman, et al. "Multivalent avimer proteins evolved by exon shuffling of a family of human receptor domains" Nat. Biotech. 23, 1556-61 (2005).

Skerra "Alternative non-antibody scaffolds for molecular recognition" Curr. Opin. Biotechnol. (2007) 18(4), 295-304.

Skerra "Anticalins as alternative binding proteins for therapeutic use" Curr. Opin. Mol. Ther. (2007) 9(4), 336-44.

Stefan, et al. "Quantification of dynamic protein complexes using *Renilla* luciferase fragment complementation applied to protein kinase A activities in vivo" Proc. Natl. Acad. Sci. USA (2008) 104(43), 16916-21.

Stumpp, et al. "DARPins: a true alternative to antibodies" Curr. Opin. Drug Discov. Devel. (2007) 10(2):153-9.

Tawfik, et al. "Man-made cell-like compartments for molecular evolution" Nature Biotechnol. (1998) 16, 652-656.

METHOD FOR THE SELECTION OF SPECIFIC AFFINITY BINDERS BY HOMOGENEOUS NONCOMPETITIVE ASSAY

This application is a continuation of U.S. application Ser. No. 12/888,188 filed Sep. 22, 2010, which claims priority to U.S. Provisional No. 61/244,770 filed Sep. 22, 2009, each of which are incorporated herein by reference in its entirety.

FIELD OF THE INVENTION

The invention generally relates to the field of immunochemistry including antibody therapy, diagnostics, and basic research and specifically relates to the area of selecting affinity molecules such as natural antibodies, including artificial antibodies, antibody mimics, and aptamers. The invention relates particularly to a method of selecting affinity molecules using a homogeneous noncompetitive assay in a high throughput process.

BACKGROUND OF THE INVENTION

Antibodies and specific alternatives are a standard tool for research product, diagnostic, and therapeutic applications. Discovery and characterization of affinity reagents for these applications can be challenging and arduous, involving antigen preparation, in vitro and/or in vivo development of binders, as well as screening and isolation of those binders. For example, mouse monoclonal antibodies are generated by immunization of mice with a purified antigen, to allow in vivo development of IgG antibodies by the B cells, and selection of an appropriate antibody by screening the expression of hybridomas (Köhler & Milstein Nature (1975) 256 (5517):495-7). More recently, antibody fragments (e.g., single chain variable fragments (scFv), and $V_HH$ domains) and artificial affinity binders (e.g., Affibodies, Monobodies, and DARPins) have been created and are developed by screening large gene libraries of potential binders with various panning technologies. These technologies have allowed the development of numerous protein scaffolds with unique affinity interaction domains that bind target epitopes.

A plethora of affinity molecule panning/screening technologies have been developed over the past decade and all share the requisite association of expressed protein with its nucleic acid coding sequence, which serves to identify the affinity binder. These technologies can be generally divided into two groups: in vivo and in vitro display. In vivo technologies are based on the introduction by viral infection or cellular transfection of a single gene into a cell, expression of the affinity binder protein from the gene, delivery of the binder to the surface of the cell or phage, selection of the affinity molecule to an immobilized target molecule, and identification of the gene associated with the affinity binder (Hoogenboom, H. R. (2005) Nature Biotech 23 (9), 1105-16). Examples of in vivo type display technologies are bacterial, yeast, mammalian, insect, and phage display.

In vitro technologies use the basic protein expression apparatus of a cell, either as a cell extract or a purified system (Shimizu, et al. Nature Biotechnology (2001) 19, 751-755), but do not require a viable cell to express the affinity binder. Therefore, the required association of coding sequence with affinity binder is through a physical bond. For ribosome display, this is done by "freezing" the ribosome at the end (stop codon) of an mRNA transcript after it has completed translating the transcript into a protein, which is also bound to the ribosome (Hanes, J. et al. (1998) Proc Natl Acad Sci USA 95(24), 14130-5). Affinity molecules to the target molecule are selected similarly to in vivo display technologies (i.e., with an immobilized target molecule) and the mRNA transcript reverse transcribed into DNA for amplification, identification, and cloning. RNA display covalently links the 3' end of an mRNA transcript to the translated affinity molecule protein using a linker, which is added to the 3' ends of the mRNA and incorporated into the affinity binder protein at its C-terminal end (Roberts, R. W., and Szostak, J. W. (1997) PNAS 94 (23), 12297-302). DNA display physically associates the affinity molecule to the DNA coding sequence, either using a DNA replication initiator protein (RepA) fused to the affinity binder (ref) or a Hae III DNA methyltransferase that specifically recognizes methylated sequences (Bertschinger & Neri Protein (2004) Eng. Des. Sel. 17 (9), 699-707). While the former can be performed in solution, the latter requires individual reactions for each protein expression event using in vitro compartmentalization.

In vitro compartmentalization (IVC) was developed in 1998 by Andrew Griffiths and Dan Tawfik (Nature Biotech. 16, 652) as an alternative to standard reaction vessels. Using cellular compartmentalization as a model, this technology facilitates the creation of minuscule aqueous solutions using water-in-oil emulsions, that is, small droplets of hydrophilic fluid exist as individual compartments in a sea of hydrophobic fluid. Droplets can be less than a micron in size (less than a femtoliter in volume) and an emulsion can have greater than $10^{10}$ droplets per ml. Griffiths and Tawfik demonstrated that a gene library distributed in a cell-free extract and compartmentalized into droplets can express their individual proteins in each droplet. In one case, the protein is an enzyme that reacts with a substrate and the technique can be used to evolve the enzyme with desired attributes. In another case, the gene is covalently bound to a bead that also contains an affinity molecule that captures the gene product (e.g., using a protein tag), thereby associating the gene with its expression product for affinity molecule selection. In addition, there is the technique noted above that uses Hae III DNA methyltransferase.

Homogeneous noncompetitive immunoassays by definition do not require physical separation of an affinity molecule bound to its target before detection. A common example of this technique is aggregation or agglutination immunoassays. Another example is Förster (or fluorescence) resonance energy transfer (FRET), which is based on the transfer of Förster energy (nonradiative transfer) from an excited fluorophore to another fluorophore that is in proximity (Valanne et al. (2005) Anal. Chim. Acta 539, 251-6). A similar method uses a bioluminescent protein, such as luciferase, to excite a proximal fluorophore (BRET), typically a fluorescent protein (Xu et al. (1999) Proc. Natl. Acad. Sci. USA 96(1), 151-6). Another homogeneous assay alternative is a luminescent oxygen-channeling chemistry (Ullman et al. (1994) Proc. Natl. Acad. Sci. USA 91 (12), 5426-30), wherein a light induced singlet oxygen generating system transfers the singlet oxygen to a chemiluminescent system in proximity. The NanoDLSay system is a single-step homogeneous assay that uses conjugated gold particles to form aggregates in the presence of an antigen (Liu et al. (2008) J. Am. Chem. Soc. 130 (9), 2780-2). Proximity ligation assay (PLA) uses two DNA single strands, one attached to each affinity molecule partner, that are complementary to a third oligonucleotide (Gullberg (2004) Proc Natl Acad Sci USA 101 (22), 8420-8424). When the affinity molecules are proximal to each other, the strands hybridize to the linker oligonucleotide in an orientation where ends (3' and 5') are next to each other and can be ligated together. The resulting DNA is amplified and quantified using Q-PCR.

Protein fragment compartmentalization (PFC) is similar to PLA in that 2 complementary molecules are fused to potentially proximal binders that interact preferentially when in proximity. In this case, the molecules are protein fragments capable of assembling into a complete and functional protein, typically an enzyme or fluorescent protein. Protein-protein interaction sensors using protein fragments were first developed by Nils Johnsson and Alexander Varshaysky using a split ubiquitin and this idea was further developed by Stephen Michnik in 1997 (Pelletier et al. (1998) J. Biomol. Tech. acc. No. 50012) as an in vivo protein-protein interaction analysis tool. The technique was used to develop an in vivo antibody (scFv) screening method by fusing one protein fragment on the antigen and the other protein fragment on a library of scFv (Mössner et al. J. Mol. Biol. (2001) 308 (2), 115-122; Koch et al. J. Mol. Biol. (2006) 357, 427-441; Secco et al. (2009) Prot. Evol. Des. Sel. 22 (5), 149-158). Recently, Panbio Diagnostics has developed a homogeneous assay for the detection of antigen or antibodies using protein fragment complementation, which they call Forced Enzyme Complementation (FEC).

Most examples of affinity binder screening by PFC are in vivo, that is, the binding reactions are compartmentalized using cells. As mentioned above, an alternative to using live cells is encapsulated cell-free extracts using IVC, preferably manipulated using microfluidics. While there are numerous examples of in vitro protein expression using IVC, only recently has this been done using microfluidic devices. Dittrich, et al. (Chembiochem. (2005) 6 (5):811-4), has recently demonstrated in vitro expression of a green fluorescent protein (red-shifted mutant) in 5 micron (~65 fL) microdroplets that were detected using confocal fluoroscopy. Few other researchers have developed this technology, preferring to use compartmentalized cell based assays (Brouzes et al. PNAS (2009) early edition).

SUMMARY

In some embodiments, the present invention provides a method for screening specific affinity molecules to target molecules using a homogeneous noncompetitive assay. In some embodiments, the method comprises use of reagents to perform a homogeneous non-competitive assay, in which candidate affinity molecules are used to conduct the homogeneous non-competitive assay in order to identify candidate affinity molecules with affinity for the target as indicated by a positive result in the homogeneous non-competitive assay. In some embodiments, the affinity molecules are native antibodies, antibody fragments, artificial antibody scaffolds, peptides, or nucleic acids. In some embodiments, the native antibodies are IgG, IgM, IgA, or IgE molecules; the antibody fragments include $(Fab)_2$, Fab, and scFv; and the artificial antibody scaffolds include Nanobodies, Affibodies, Anticalins, DARPins, Monobodies, Avimers, and Microbodies. In some embodiments, peptides are greater than three amino acids, consist of either natural or non-natural amino acids, and include peptide aptamers; the peptides are covalently attached to a carrier molecule. In some embodiments, the nucleic acid includes nucleic acid aptamers and peptide nucleic acids (PNA). In some embodiments, the affinity binders are expressed from genes or chemically synthesized. In some embodiments, the affinity molecules are comprised of a tyrosine/serine binary-code interface or a tyrosine/serine/X amino acid tertiary-code interface. In some embodiments, two or more affinity molecules are required to bind to at least 2 different epitopes of a target molecule. In some embodiments, the binding of the first known affinity molecule and a second unknown affinity molecule is an individual reaction performed in an individual vessel. In some embodiments, the individual vessel is a single reaction tube or a well of microtiter plate. In some embodiments, the individual vessels are water microdroplets, wherein water microdroplets can be created by water-in-oil technology. In some embodiments, the water microdroplets are created using micro- or nanofluidic devices, wherein a micro- or nanofluidic device is used to manipulate microdroplets to mix reagents, perform reactions, heat, cool, detect and analyze assay output, and sort into various collection systems. In some embodiments, the reaction vessels are in vivo cells including bacteria, archaebacteria, fungal, insect, and mammalian cells.

In some embodiments, one affinity molecule is associated with a protein fragment via a flexible linker that complements another protein fragment associated with the second affinity molecule via a flexible linker. In some embodiments, complementation of the protein fragments associated with affinity molecules generates a measurable signal. In some embodiments, the measurable signal includes color, fluorescence, and bioluminescence. In some embodiments, the affinity molecules are in proximity when bound to the target to allow complementation of associated protein fragments. In some embodiments, one affinity molecule is associated with a donor fluorophore via a linker that can transfer Forster energy to an acceptor fluorophore that is linked via a linker to the second affinity molecule. In some embodiments, one affinity molecule is associated with a bioluminescent protein via a linker that can transfer Förster energy to an acceptor fluorophore that is linked via a linker to the second affinity molecule. In some embodiments, one affinity molecule is associated with a light induced singlet oxygen generating system via a linker and the second affinity molecule is a singlet oxygen dependent chemiluminescent system (luminescent oxygen channeling). In some embodiments, the affinity molecules are associated with gold particles conjugated with anti-epitope antibodies that aggregate when the reference affinity molecule and the unknown affinity molecule (each with a different epitope tag) bind.

In some embodiments, the first affinity molecule is the reference affinity molecule and is known to bind the target with relatively high affinity while the binding affinity of the second affinity molecule is not known, but is determined by the homogeneous noncompetitive assay. In some embodiments, the first affinity molecule has affinity for an epitope tag that is added to the target, wherein the epitope tag is polypeptide expressed along with the protein affinity molecule, including, but not limited to, His-tag, FLAG-tag, V5-tag, HA-tag, and c-myc-tag. In some embodiments, the epitope tag is covalently bonded to the target. In some embodiments, the second affinity molecule is derived from a library of potential affinity molecules.

In some embodiments, the target molecule may be a protein, glycoprotein, phosphoprotein, other post-modification protein, protein complex, nucleic acid, protein:nucleic acid complex, carbohydrate, lipid complex, organic and inorganic molecule, including natural and synthetic versions of any such molecules. The target or target molecules may comprise a single protein or other biomolecule or multiple molecules (e.g., in a multi-molecular complex). For example, in some embodiments, affinity molecules are used to simultaneously bind two or more molecules that are in proximity to one other, to, for example, detect such proximity.

Embodiments of the present invention further provide methods of using the complexes in therapeutic, diagnostic, and basic or applied research settings (e.g., drug screening applications).

BRIEF DESCRIPTION OF THE DRAWINGS

The foregoing summary and detailed description is better understood when read in conjunction with the accompanying drawings which are included by way of example and not by way of limitation.

DEFINITIONS

Figure 1:
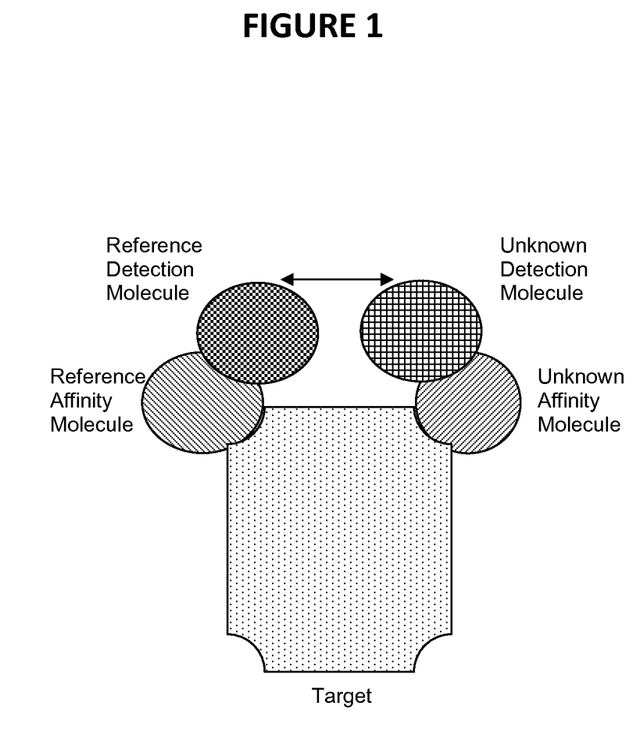
FIG. 1 shows a cartoon representing a simple design of some embodiments, showing an affinity complex comprising a target and two affinity molecules with attached complementary detection molecules. The target is represented by the spotted square with corner knockouts, which represent epitopes of the target. The reference affinity molecule (oval with downward diagonal) binds to one epitope and is associated to a detection molecule (oval with checkerboard). The unknown affinity molecule (oval with downward diagonal) binds to another epitope of the target and is associated to a complementary detection molecule (oval with squares). The 2 complementary detection molecules function only when in proximity.
Figure 2:
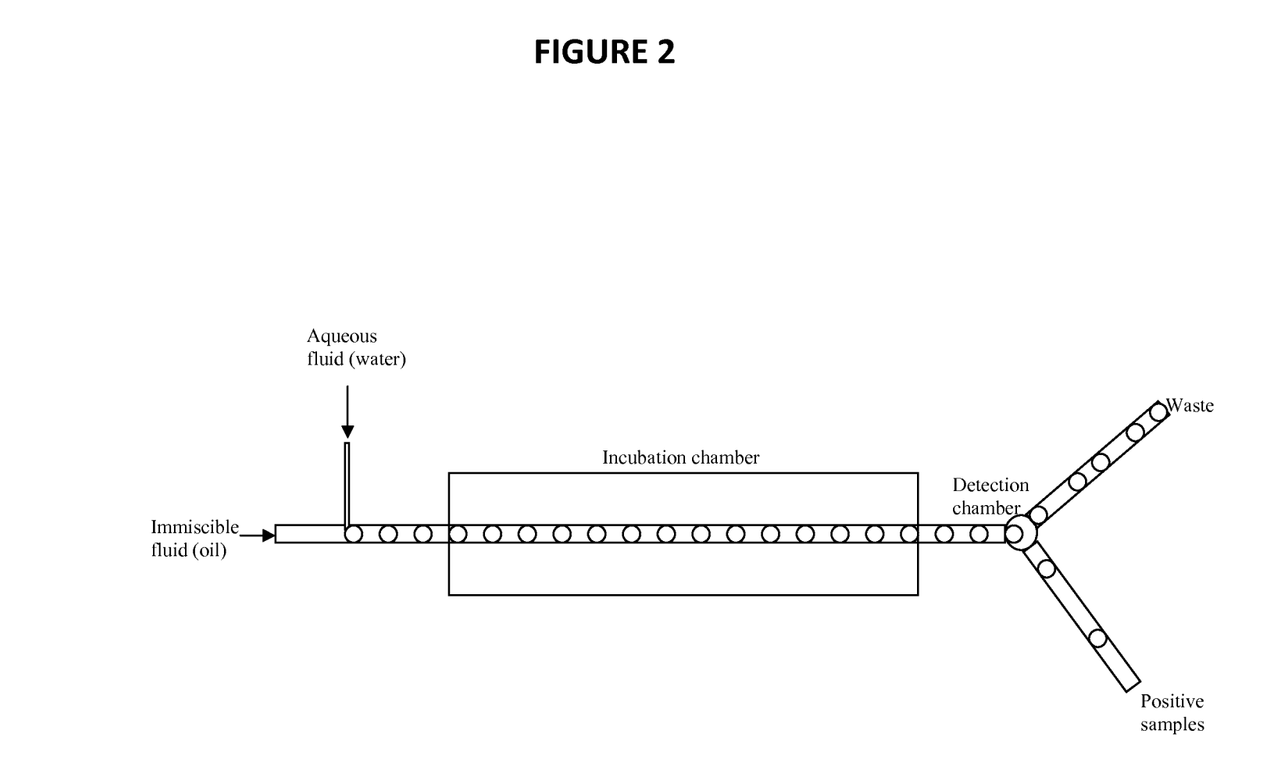
FIG. 2 shows an example of a microfluidic device. An immiscible fluid is pumped through the pathway of the device and an aqueous fluid containing an affinity molecule gene library in a cell-free translation solution is injected forming microdroplets. Upon protein expression, the affinity molecules bind to a target, the detection molecules are allowed to interact, and detected in a sorting chamber. Positive samples are gated to a collection bin while negative microdroplets are gated to the waste.

As used herein, the term "about" means encompassing plus or minus 10%. For example, about 200 nucleotides refers to a range encompassing between 180 and 220 nucleotides.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to nucleic acid sequences that are not found naturally associated with the gene sequences in the chromosome or are associated with portions of the chromosome not found in nature (e.g., genes expressed in loci where the gene is not normally expressed).

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5 (carboxyhydroxyl-methyl)uracil, 5-fluorouracil, 5 bromouracil, 5-carboxymethylaminomethyl 2 thiouracil, 5 carboxymethyl-aminomethyluracil, dihydrouracil, inosine, N6 isopentenyladenine, 1 methyladenine, 1-methylpseudouracil, 1 methylguanine, 1 methylinosine, 2,2-dimethyl-guanine, 2 methyladenine, 2 methylguanine, 3-methyl-cytosine, 5 methylcytosine, N6 methyladenine, 7 methylguanine, 5 methylaminomethyluracil, 5-methoxy-amino-methyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxyacetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

As used herein, the term "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth Enzymol.* 68:90-99; the phosphodiester method of Brown et al. (1979) *Meth Enzymol.* 68:109-151; the diethylphosphoramidite method of Beaucage et al. (1981) *Tetrahedron Lett.* 22:1859-1862; the triester method of Matteucci et al. (1981) *J Am Chem. Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein, the term "affinity complex" refers to an interacting multicomponent collection of molecules that specifically interacts through interactions (e.g. hydrogen bonding, Van der Waals forces, electrostatic forces, hydrophobic forces, etc.) with a target molecule.

As used herein, the term "affinity molecule" refers to any molecule that specifically interacts through interactions (e.g.

hydrogen bonding, Van der Waals forces, electrostatic forces, hydrophobic forces, etc.) with a target molecule.

As used herein, the term "artificial antibody" or "antibody mimic" refers to any non-immunoglobulin molecule or molecular complex that is created to specifically interact with a target molecule.

As used herein, the term "epitope" refers to any surface region of a target molecule to which an affinity molecule binds.

As used herein, the term "discontinuous epitopes" refers to two or more surface regions of a target molecule or molecules that are separated by a defined distance.

The term "paratope" refers to the surface region of an affinity molecule that interacts with the epitope of the target molecule.

As used herein, the term "affinity" refers to the non-random interaction of two molecules. The term "affinity" refers to the strength of interactions and can be expressed quantitatively as a dissociation constant ($K_D$). One or both of the two molecules may be a peptide (e.g. antibody). Binding affinity (i.e., $K_D$) can be determined using standard techniques. For example, the affinity can be a measure of the strength of the binding of an individual epitope with an antibody molecule.

As used herein, the term "avidity" refers to the cooperative and synergistic bonding of two or more molecules. "Avidity" refers to the overall stability of the complex between two or more populations of molecules, that is, the functional combining strength of an interaction.

As used herein, the term "protein fragment complementation" refers to a protein that can be fragmented into two or more parts so that when the fragments are in proximity they reform the original functional protein.

As used herein, the term "in vitro compartmentalization" refers to a method of creating cell-like compartments using emulsion (water-in-oil) technology.

As used herein, the term "Förster resonance energy transfer" or "FRET" refers to a process in which energy is transferred between an excited fluorophore (donor) and an acceptor fluorophore.

As used herein, the term "Bioluminescence resonance energy transfer" or "BRET" refers to a process in which energy is transferred between a bioluminescent protein and an acceptor fluorophore.

DETAILED DESCRIPTION OF EMBODIMENTS

In some embodiments, the present invention provides a method for screening specific affinity molecules to target molecules using a homogeneous noncompetitive assay in a high throughput process. In some embodiments, the present invention provides compositions, systems, and methods related to the screening of specific affinity molecules to target molecules using a homogeneous noncompetitive assay in a high throughput process. In some embodiments, the method comprises use of reagents to perform a homogeneous non-competitive assay, in which candidate affinity molecules are used to conduct the homogeneous non-competitive assay in order to identify candidate affinity molecules with affinity for the target as indicated by a positive result in the homogeneous non-competitive assay.

In some embodiments, a target molecule contains two or more epitopes to which the affinity binders can interact. In some embodiments, the epitopes are discontinuous. In some embodiments, the affinity molecules recognize the same epitopes. In some embodiments, the affinity molecules recognize different epitopes. In some embodiments, the affinity molecules recognize multiplexed targets.

Affinity Molecules

In some embodiments, the affinity molecule comprises or consists of a scaffold that has a region known as a paratope or a target epitope interaction domain and a detection molecule connected via a linker. In some embodiments, the paratope and detection molecule are situated to allow interaction with a target epitope and a freedom of the detection molecule. In some embodiments, each affinity molecule can comprise or consist of the same scaffold. In some embodiments, each affinity molecule can comprise or consist of different scaffolds.

In some embodiments, affinity molecules can be any antibody, antibody fragment, scaffold or molecular construct that has a paratope domain or region and a detection molecule domain or region. For example, IgG antibodies known to interact with a single target can used with a molecule that interacts with each Fc domain of the IgG (such as Protein A or G) and contains the detection molecule. In some embodiments, Fab fragments of an IgG antibody are employed as the affinity molecule and can be linked to the detection molecule through the constant domains (CL and CH1) of the molecule. In some embodiments, single chain fragments of the variable domains (scFv) are employed due to their increased stability. In some embodiments, the smaller size of the VHH domain of camelids (Nanobodies) is a preferred affinity molecule.

In some embodiments, the affinity molecule is a monobody (fibronectin type III domain) derived from a human cell surface protein. This scaffold is structurally similar to antibody variable domains, but does not contain disulfide bonds that can hinder expression in prokaryotic systems. In some embodiments, monobodies have a molecular weight of ~10,000 Daltons, they are very soluble, and thermally and proteolytically stable. In some embodiments, the monobody scaffold contains three loops (BC, DE, and FG loops) that can be collectively employed as a paratope, similar to the CDR regions of an immunoglobulin. The polar opposite end of the paratope region contains three additional loops (AB, CD, and EF loops). In some embodiments, the N-terminal, C-terminal, or AB, CD, and EF loops can be employed as a linker to the detection molecule. In some embodiments, other linkers can be used, such as an abbreviated rPEG.

In some embodiments, the affinity molecule is a DARPin (designed ankyrin repeat protein) that is derived from a large class of repeat proteins found in various cellular sections in a variety of species. Each repeat consists of 33 amino acid residues that form a beta-turn followed by two anti-parallel helices and a randomized loop that is joined to the beta-turn of the next repeat and functions to "stack" the repeats generating a very stable hydrophobic core. In some embodiments, the loop and beta-turn sequences are involved in the paratope of the molecule. In some embodiments, residues of the helices can contribute to the paratope. In some embodiments, the combination of the loop and beta-turn sequences and the residues of the helices generate a broad paratope interface. In some embodiments, three or more of these repeats are created to generate a molecule with very high affinity. In some embodiments, the ends of the repeats are "capped" to preserve the hydrophobic core, increase its solubility and stability, and can be used for labeling or immobilization. In some embodiments, N-terminal and C-terminal caps are employed as linkers to the detection molecule.

In some embodiments, the affinity molecule is an Affibody (the Z domain of Staphylococcal protein A) that comprises or consists of 58 amino acids arranged as a bundle of 3 anti-parallel alpha helices. In some embodiments, the small size of the affibody molecule provides easier expression and solubility in prokaryotic systems. In some embodiments, the affibody polypeptide is chemically synthesized then folded, which allows the introduction of non-canonical amino acids in the interaction domain or the addition of labels or reactive groups. In some embodiments, the interaction domain comprises or consists of 13 amino acid residues that are randomized to generate a library from which an affinity molecule is panned. In some embodiments, binding affinities for affibodies and their substrates are in the nanomolar range.

In some embodiments, the affinity molecule is a Microbody (Nascacell Technologies). In some embodiments, a microbody is based on natural cysteine-knot microproteins and cyclical knottins. In some embodiments, Microbodies are small (28 to 45 amino acids), yet very stable due to three disulfide bonds within the structure, which allows the display of a single peptide loop up to 20 amino acids. In some embodiments, microbodies are very soluble and are expressed from bacteria or synthesized by chemical means then properly folded. In some embodiments, the stability and solubility of these proteins provides alternative therapeutic delivery modes to the standard injection of most biologicals. In some embodiments, a very similar molecule called a Versabody (Amunix), acts as a primary affinity molecule. In some embodiments, a Versabody is a very small high disulfide density scaffold based on natural biopharmaceuticals, such as scorpion toxin. Versabodies are extremely stable, soluble, and non-immunogenic.

In some embodiments, the affinity molecule is an Anticalin, an Avimer or the domain A of an Avimer, a thioredoxin, an ubiquitin, a gamma-crystallin, CTLA-4 (Evibody), or other recombinant artificial antibodies. In some embodiments, a primary affinity molecule is any molecule capable of binding a target with a suitable affinity.

In some embodiments, the affinity molecule is a nucleic acid or peptide aptamer, wherein the nucleic acid or peptide contains a target affinity domain and a detection molecule affinity domain.

Paratopes of Affinity Molecules

In some embodiments, the binding interaction of a paratope to its epitope is based upon a combination of molecular contacts that together account for the affinity strength (e.g. Van der Waals interactions, hydrogen bonding, and hydrophobic interactions), specific amino acid side groups of the paratope polypeptide form bonds with amino acid side groups of the epitope polypeptide. In some embodiments, a portion of the amino acids in the paratope function as structural support. In some embodiments, antibody mimics have a single polypeptide paratope, such as Affibodies and Versabodies. In these embodiments, the sum of those interactions determines the affinity. In some embodiments, affinity molecules comprise multiple polypeptide loops or CDRs (complementarity determining regions), such as fibronectin Type III domains, ankyrin repeats, and IgG molecules. These embodiments demonstrate additional number and spacing of those interactions. In some embodiments, the structure of the paratope should be adaptable to fit the epitope. In some embodiments, the paratope has enough flexibility to form bonds with the epitope without introducing intramolecular strain. In some embodiments, a large number of affinity molecules are be screened (e.g., in a binding assay) to achieve a suitable structure.

In some embodiments, only moderate affinity interactions are required. In some embodiments, only moderate affinity interactions are preferred. In embodiments, increased effectiveness of screening libraries is achieved when moderate affinity is sought. In some embodiments, binary- or tertiary-code library systems reduce the size of the libraries, increase their effectiveness, and further simplify the process. In some embodiments, the basis of the binary-code interface within affinity molecules is that effective affinity binders can be generated by using only 2 amino acids, tyrosine and serine (e.g. fibronectin type III domains that were developed using the Tyr/Ser binary-code interface demonstrated affinities to 3 different proteins of 5 to 90 nM (Koide, A., et al., *Proc. Nat. Acad. Sci.* 104, 6632-6637, herein incorporated by reference in its entirety)). In some embodiments, a nanomolar affinity level, which can be achieved in binary-code interface, is very effective in an affinity complex where the binding affinities are multiplied by the linkage of the affinity molecules. In some embodiments, the combination of a simplified binary-code interface library system and a cooperative affinity complex system greatly reduces the time and resources necessary to development high affinity and specific affinity complexes.

Detection Molecules

In some embodiments, the detection molecule is a protein fragment complementation system, wherein one protein fragment fused to one affinity molecule is complementary to another protein fragment fused to the other affinity molecule and complementation of protein fragments generates a measurable signal (protein fragment complementation assay). In some embodiments, the complementary protein fragments generate an active enzyme.

In some embodiments, the active enzyme is β-lactamase that can generate a colored product from a substrate such as nitrocefin, a fluorescent product from the substrate such as Fluorocillin Green, or a bioluminescent product (in combination with firefly luciferase) from a substrate such as Bluco (β-lactam-D-luciferin).

In some embodiments, the active enzyme is a luciferase that can generate bioluminescence from a substrate such as D-luciferin for firefly luciferase and coelenterazine luciferin for renilla and gaussia luciferases (ref).

In some embodiments, the complementary protein fragments generate a fluorophore such as green fluorescent protein, red fluorescent protein, or mutants of these proteins.

In some embodiments, the detection molecule is a donor or acceptor fluorophore that can be used in a Förster resonance energy transfer (FRET) assay. For example, one affinity molecule would be fused to the donor fluorophore via a linker and the second affinity molecule would be fused with the acceptor fluorophore via a linker. In some embodiments, the donor molecule is cyan fluorescent protein (CFP) and the acceptor molecule is yellow fluorescent protein. In some embodiments, the donor molecule is CyPet and the acceptor molecule is YPet. In some embodiments, the donor molecule is TagGFP and the acceptor molecule is TagRFP. In some embodiments, each affinity molecule fluorophore fusion protein contains domains that have complimentary affinity, wherein proximal donor and acceptor fluorophores are spatially oriented to allow efficient energy transfer. In some embodiments, the complimentary affinity domains are leucine zipper or other coiled-coil domains. In some embodiments, the complimentary affinity domains are affinity molecules designed for expressly this purpose.

In some embodiments, the donor and/or acceptor fluorophore is a small organic or inorganic molecule that is fused to a polypeptide or other molecule that has specific affinity for an expressed polypeptide fused to the affinity molecule. For example, fluorescein isothiocyanate can be conjugated to the end of the K-coil of a coiled-coil dimer that is complementary to the E-coil that is fused to the affinity molecule as it is expressed. In some embodiments, the fluorophore is conjugated to a chelated metal, such as nickel or copper, that binds a HisTag (4-10 histidines) fused to the affinity molecule as it is expressed. In some embodiments, the fluorophore is conjugated to streptavidin that binds to a 15 amino acid Nanotag fused to the affinity molecule as it is expressed.

In some embodiments, the fluorophore is conjugated to an affinity molecule that has affinity for the expressed affinity molecule (that has affinity for the target). In some embodiments, the affinity molecule to the target is fused with another affinity molecule that has affinity for the fluorophore or a conjugated fluorophore. In some embodiments, the organic fluorophore is a derivative of fluorescein, rhodamine, Alexa Fluors (Invitrogen), CyDye Fluors (GE Healthcare Life Sciences), DyLight Fluors (Dyomics GmbH), HiLyte Fluors (Anaspec) and the IRDye Near Infrared Fluors (Li-Cor).

In some embodiments, the inorganic fluorophore is a derivative of a rare earth metal chelate or cryptate (crown ether) such as lanthanium, terbium, samarium, dysprosium, or europium. In some embodiments, the fluorophore is a latex bead containing more than one fluorophore. In some embodiments, the fluorophore is a phycobiliprotein, such as R-phycoerythrin or allophycocyanin. In some embodiments, the fluorophore is a quantum dot.

In some embodiments, fluorophores are linked to either a NHS ester reactive group (reacts with ε-amine of lysine and the α-amine of the polypeptide N-terminal) or a maleimide reactive group (reacts with reduced sulfhydryl of cysteine). In some embodiments, labeling proteins non-specifically, especially small polypeptides can potentially interfere with their function. In some embodiments, it is important to demonstrate no loss of utility of the affinity molecule. In some embodiments, if the affinity molecule does not have a cysteine in the polypeptide sequence (such as an Affibody or fibronectin scaffold), a cysteine can be introduced at the C-terminal and specifically labeled with any maleimide fluorophore.

In some embodiments, the FRET assay is time-resolved (TR-FRET), wherein detection of fluorescence of the acceptor fluorophore is determined after a short delay (for example, 100 μsec) after excitation of the donor fluorophore, that is, the fluorescence of the donor has diminished significantly and the lifetime of the acceptor is sufficiently extended to measure its fluorescence.

In some embodiments, the donor detection molecule is a bioluminescent enzyme that can transfer resonance energy (BRET). For example, a luciferase enzyme typically generates light upon oxidation of its substrate, but can also transfer the energy to a fluorophore that is in proximity. In some embodiments, the bioluminescent enzyme is expressed as a fusion protein with one of the affinity molecules. In some embodiments, the bioluminescent protein is firefly, renilla, or gaussia luciferase. In some embodiments, the acceptor fluorophore is a fluorescent protein that is fused to an affinity molecule. In some embodiments, the acceptor fluorophore is an organic or inorganic In some embodiments, the bioluminescent enzyme is fused to a polypeptide or other molecule that has specific affinity for an expressed polypeptide fused to the affinity molecule. For example, firefly luciferase can be fused to the K-coil of a coiled-coil dimer that is complementary to the E-coil that is fused to the affinity molecule as it is expressed. In some embodiments, the bioluminescent enzyme is conjugated to a chelated metal, such as nickel or copper, that binds a HisTag (4-10 histidines) fused to the affinity molecule as it is expressed. In some embodiments, the bioluminescent enzyme is conjugated or fused to an affinity molecule that has affinity for the expressed affinity molecule (that has affinity for the target). In some embodiments, the affinity molecule to the target is fused with another affinity molecule that has affinity for the bioluminescent enzyme. In some embodiments, the acceptor fluorophore is protein expressed as a fusion protein with one of the affinity molecules such as GFP, YFP, and RFP. In some embodiments, the acceptor fluorophore is an organic fluorophore, inorganic fluorophore, or quantum dot.

In some embodiments, the donor detection molecule is a light induced singlet oxygen generating system and the acceptor detection molecule is a chemiluminescent system that is excited by singlet oxygen (luminescent oxygen channeling).

In some embodiments, the detection system is a dynamic light scattering assay, wherein the detection molecules are gold nanoparticles conjugate to affinity molecules with affinity for either reference of unknown affinity molecule. For example, a portion of gold nanoparticles can be conjugated with anti-His tag antibodies and another portion with anti-FLAG antibodies. Aggregation occurs in the presence of the target when both the affinity molecule expressing the His tag and the affinity molecule expressing the FLAG tag bind the target.

In some embodiments, the detection molecule is covalently linked to the affinity molecule via a flexible polymer such as a polypeptide (e.g. glycine/serine polypeptides), a nucleic acid strand, polyethylene glycol, and peptide nucleic acid (PNA) that has sufficient degree of freedom to allow the interaction of the secondary affinity molecules with the primary affinity molecules. In some embodiments, the affinity molecules are linked, either directly or linked via a suitable linker. The present invention is not limited to any particular linker group. Indeed, a variety of linker groups are contemplated, suitable linkers could comprise, but are not limited to, alkyl groups, ether, polyether, alkyl amide linker, a peptide linker, a modified peptide linker, a Poly(ethylene glycol) (PEG) linker, a streptavidin-biotin or avidin-biotin linker, polyaminoacids (eg. polylysine), functionalised PEG, polysaccharides, glycosaminoglycans, dendritic polymers such as described in WO93/06868 and by Tomalia et al. in Angew. Chem. Int. Ed. Engl. 29:138-175 (1990), PEG-chelant polymers such as described in W94/08629, WO94/09056 and WO96/26754, oligonucleotide linker, phospholipid derivatives, alkenyl chains, alkynyl chains, disulfide, or a combination thereof.

In some embodiments the linker comprises a single chain connecting the detection molecule to the affinity molecule. In some embodiments, there are multiple linkers connecting the detection molecule to the affinity molecule. In some embodiments, a linker may connect multiple the detection molecules to the affinity molecule. In some embodiments, a linker attaches an additional functional portion to affinity molecule. In some embodiments, a linker may be branched, connecting more than two detection molecules to the affinity molecule. In some embodiments, the linker may be flexible, or rigid. In some embodiments, the linker of the present invention is cleavable or selectively cleavable. In some embodiments, the linker is cleavable under at least one set of conditions, while not being substantially cleaved (e.g. approximately 50%, 60%, 70%, 80%, 90%, 95%, 99%, or greater remains uncleaved) under another set (or other sets) of conditions. In some embodiments, the linker is susceptible to enzymatic cleavage (e.g. proteolysis). In some embodiments, the enzymatic cleavage is site specific (e.g. sequence specific). In some embodiments, the enzymatic cleavage is at a random site along the linker. In some embodiments, the enzymatic cleavage may occur at multiple random sites along the linker. In some embodiments, the linker is susceptible to cleavage under specific conditions relating to pH, temperature, oxidation, reduction, UV exposure, exposure to radical oxygen species, chemical exposure, light exposure (e.g. photo-cleavable), etc.

In some embodiments, detection molecules are prepared by any suitable method. In some embodiments, IgG antibodies are used as affinity molecules and can be linked via their reduced thiol groups, preferably using a crosslinking system from SoluLink. In some embodiments, one part of the anti-Fc IgG/Fab is labeled with MHPH (3-N-Maleimido-6-hydraziniumpyridine hydrochloride) and the other part with MTFB (Maleimido trioxa-6-formyl benzamide). In some embodiments, the hydrazine moiety of the MHPH-modified molecules react with 4-formylbenzamide of the MTFB-modified molecules to form stable bis-arylhydrazone-mediated conjugates. In some embodiments, alternative methods for crosslinking proteins, known to those skilled in the art, are utilized. In some embodiments, an oligonucleotide can be synthesized with chemically reactive moieties (for example, a maleimide) on each end that would react with the secondary affinity molecule. In some embodiments, each molecule could be conjugated to an oligonucleotide, one with a 3' is free and the other with a 5' free so that the two strands can be ligated. In some embodiments, any suitable methods to link the secondary affinity molecules would also be appropriate so long as the linker has flexibility to allow interaction of the secondary affinity molecules.

Target Molecules

In some embodiments, the target may be a protein, nucleic acid, carbohydrate, lipid, or other cell component. In some embodiments, the protein may be native or denatured, modified (such as glyco- or phosphoproteins), part of a complex with other proteins, nucleic acids, or lipids (such as a lipid micelle), or part of a cell (or cell debris). In some embodiments, the nucleic acid may be DNA (single or double stranded), RNA (message, ribosomal, transfer, transfer-message, small interfering, short hairpin, micro, piwi-interactive), or PNA (peptide nucleic acid). In some embodiments, the carbohydrate may be any number of polysaccharides including glycogen, cellulose, and chitin. In some embodiments, the lipid may be a polyglyceride, wax, steroid, vitamin, or other natural hydrophobic molecules. In some embodiments, the target may be native (natural) or recombinant, expressed, transcribed, or synthesized, purified or part of a crude mixture, and with or without an epitope tag.

In some embodiments, the target may be a synthetic molecule, organic or inorganic, particle, or polymer.

Assay Screening

In some embodiments, the method of screening for an affinity molecule includes a target molecule, a reference affinity molecule that is known to bind the target molecule with a known affinity, and an unknown affinity molecule. In some embodiments, the reference affinity molecule has affinity for a specific epitope on the target or an epitope tag added to the target. In some embodiments, the coding sequence (either DNA or mRNA) for the reference affinity molecule (when it is a protein) is fused to the coding sequence of the detection molecule (when it is a protein) and is expressed in the screening reaction using a cell-free translation. In some embodiments, fusions of affinity and detection molecules is expressed in a separate reaction, purified, and added to the screening assay. In some embodiments, affinity and detection molecules are chemically conjugated in a separate reaction, purified, and added to the screening assay.

In some embodiments, the affinity molecule is fused or conjugated to a secondary affinity molecule that has affinity for the detection molecule or the detection molecule may be fused or conjugated to a secondary affinity molecule that has affinity for the affinity molecule, and both the affinity and detection molecules are added to the screening assay. For example, a monobody that has affinity for a target protein is expressed with 10 histidine amino acids at the C-terminus and purified. This protein is mixed with a donor fluorophore conjugated to a nickel chelate complex that has affinity for the histidine tail and the entire complex is used in a FRET screening assay. This complex can be used for either the reference affinity molecule or the unknown affinity molecule, but not both in the same reaction.

In some embodiments, the unknown affinity molecule is prepared in the same way as the reference affinity molecule and added to the screening assay containing the target and the reference affinity molecules in a single reaction. In some embodiments, numerous unknown affinity molecules are prepared and added to a multi-well plate containing the target and the reference affinity molecules in a multiplexed screening assay. In some embodiments, a gene coding library of unknown affinity molecules are mixed with the target molecule and the reference affinity molecule (or the gene code for the reference affinity molecule) with its detection molecule in a cell-free extract capable of translating the gene library and the mixture is separated into microdroplets that are individual reactions. In some embodiments, a microfluidic device is used to create the microdroplets, merge and mix droplets, optimally heat the reactions (both translation and enzymatic assay if required), detect the output of the detection molecules (color, fluorescence, or bioluminescence light), sort and collect those droplets that exhibit a positive signal. In some embodiments, the microfluidic device amplifies the DNA in each droplet by polymerase chain reaction (PCR), or other amplification techniques, creating sufficient DNA to identify the gene sequence that codes for the positive binding reaction. In some embodiments, the microfluidic device (instrument) is a RainDance Technology instrument capable of creating, processing, and analyzing 3000 droplets per second, which would allow the screening of over 10 million reactions per hour ($2.6 \times 10^8$ per day).

Epitope Mapping

In some embodiments, a target molecule is mixed with various combinations of affinity molecules known to have affinity for the target and, in association with their detection molecules, determined which combination produces a negative result indicating that both affinity molecules have affinity for the same epitope. For example, a gene library that has been screened for affinity molecules to a target molecule generates 25 positive clones, each of which is PCR amplified with both the detection molecule coding sequences and expressed in cell-free extract to generate the specific affinity molecules fused with a reference detection molecule and its complement detection molecule. Affinity molecule #1 with its reference detection molecule is mixed with the target molecule and placed in each well of the first row (24 wells) of a 384 well plate to which affinity molecule #2 with its complementary detection molecule has been added to well A1, affinity molecule #3 with its complementary detection molecule has been added to well A2, and so on. The second row contains affinity molecule #2 with its reference detection molecule, the third row with #3 and so on. Positive signals indicate affinity binding of both affinity molecules to the target while negative signals indicate conflicting binding sites.

Systems and Kits

The present invention further provides systems and kits (e.g., commercial therapeutic, diagnostic, or research products, reaction mixtures, etc.) that contain one or more or all components sufficient, necessary, or useful to practice any of the methods described herein. These systems and kits may

EXPERIMENTAL

Example 1

Exemplary Use

The first example demonstrates homogeneous FRET analysis and its implementation in a microfluidic device. A small His tag labeled protein target is mixed with HiLyte Fluor™ 488 conjugated mouse anti-His tag monoclonal antibody and a known anti-target antibody (IgG) labeled with HiLyte Fluor™ 555 in a cuvette tube and the fluorescence at ~600 nm determined when exciting the solution at ~500 nm (FRET). The same binding reaction is loaded into a microfluidic device set up to measure FRET fluorescence in the same way. Next, each component is loaded into individual compartments of the microfluidic device, droplets created, merged, and mixed in line, and the FRET fluorescence determined.

Example 2

Exemplary Use of Protein Fragment Complementation

The second example demonstrates utility of complementary renilla protein fragments fused to monobody affinity molecules via a peptide linker. A protein target is chosen for which the protein is available and the monobodies exist. The coding sequence for at least 2 monobodies is cloned into a cassette containing either the N-terminal renilla peptide or the C-terminal peptide, both using a ser/gly linker. The target protein, N-terminal renilla monobody, and C-terminal renilla monobody is mixed, added to renilla Luciferase Assay Reagent (Promega), and the bioluminescence measured using a luminometer. The same binding reaction is loaded into a microfluidic device set up to measure bioluminescence in the same way. Next, each component is loaded into individual compartments of the microfluidic device, droplets created, merged, and mixed in line, and the bioluminescence determined. Finally, a gene library of C-terminal (or N-terminal) renilla monobodies coding for various peptide sequences at the BC and FG domains of the monobody is screened for binding to the target using the known renilla monobody as the reference.

Example 3

Exemplary Use of BRET

The third example demonstrates utility of a BRET system for screening affinity molecules. A protein target is chosen for which the protein is available and the monobodies exist. The coding sequence for one of the monobodies is cloned into a cassette containing a renilla luciferase sequence and the coding sequence for the other monobody is coned into a cassette containing a red fluorescent protein (RFP). The target protein, renilla monobody, and RFP monobody is mixed, added to renilla Luciferase Assay Reagent (Promega), and the fluorescence of the RFP measured using a near infrared light detector. The same binding reaction is loaded into a microfluidic device set up to measure bioluminescence in the same way. Next, each component is loaded into individual compartments of the microfluidic device, droplets created, merged, and mixed in line, and the bioluminescence determined. Finally, a gene library of C-terminal (or N-terminal) renilla monobodies coding for various peptide sequences at the BC and FG domains of the monobody is screened for binding to the target using the known renilla monobody as the reference.

REFERENCES

The following references are herein incorporated by reference in their entireties:

Köhler & Milstein Nature (1975) 256(5517):495-7
Hoogenboom (2005) Nature Biotech 23(9), 1105-16
Handbook of Therapeutic Antibodies, 2007, ed. Stefan Dubel, Wiley-VCH
Nuttall & Walsh. Curr. Opin. Pharmacol. (2008) 8(5), 609-15.
Binz et al. Nat. Biotech. (2005) 23(10), 1257-68
Hanes et al. Proc Natl Acad Sci USA (1998) 95(24), 14130-5
Roberts & Szostak PNAS (1997) 94(23), 12297-302
Bertschinger & Neri Protein Eng. Des. Sel. (2004) 17(9), 699-707
Valanne et al. Anal. Chim. Acta (2005) 539, 251-6
Xu et al. Proc. Natl. Acad. Sci. USA (1999) 96(1), 151-6
Ullman et al. Proc. Natl. Acad. Sci. USA (1994) 91 (12), 5426-30
Liu et al. J. Am. Chem. Soc., (2008) 130 (9), 2780-2.
Gullberg Proc Natl Acad Sci USA (2004) 101 (22), 8420-8424
Skerra. Curr. Opin. Biotechnol. (2007) 18(4), 295-304.
Hogbom et al. Proc. Nat. Acad. Sci. (2003) 100(6), 3191-6.
Skerra. Curr. Opin. Mol. Ther. (2007) 9(4), 336-44.
Silverman et al. (2005) Nat. Biotech. 23, 1556-61.
Koide et al. J. Mol. Biol. (1998) 284(4):1141-51.
Stumpp & Amstutz. Curr. Opin. Drug Discov. Devel. (2007) 10(2):153-9.
Roovers et al. Curr. Opin. Mol. Ther. (2007) 9(4), 327-35.
Nuttall, S D, et al., Proteins (1999) 36, 217-27.
Kolmar. FEBS J. (2008) 275(11), 2684-90.
Sergeeva et al. Adv. Drug Deliv. Rev. (2006) 58(15), 1622-1654
Rothe et al. The FASEB J. (2006) 20, 1599-1610.
Thie et al. Curr. Pharm. Biotechnol. (2008) 9(6), 439-46.
Sidhu & Koide. Curr. Opin. Struct. Biol. (2007) 17(4), 481-7.
Gai & Wittrup. Curr. Opin. Struct. Biol. (2007) 17(4), 467-73.
Daugherty. Curr. Opin. Struct. Biol. (2007) 17(4), 474-80.
He & Khan, F. Expert Rev. Proteomics (2005) 2(3), 421-30.
Liu et al. Meth. Enzymol. (2000) 318, 268-93.
Ciruela. Curr. Opin. Biotechnol. (2008) 19(4), 338-43.
Bailon & Won. Expert Opin. Drug Deliv. (2009) 6(1), 1-16.
Porcheddu & Giacomelli. Curr. Med. Chem. (2005) 12(22), 2561-99.
Gullberg et al. Curr. Opin. Biotechnol. (2003) 14(1), 82-6.
Thøgersen & Holldack. Innovations in Pharmaceutical Technology: Drug Discovery (2006) vol. February, p. 27-31
Lamla & Erdmann. Protein Expr. Purif. (2004) 33(1), 39-47.
Ohiro et al Anal. Biochem. (2007) 360, 266-272
Arai, J. Biosci. Bioeng. (2002) 94(4), 362-364
Yu. Adv. Drug Deliv. Rev. (2002) 54(8), 1113-29
Shimizu, et al. Nature Biotechnology (2001) 19, 751-755
Koide et al. Proc. Nat. Acad. Sci. (2007) 104(16), 6632-6637
Gilbreth. J. Mol. Biol. (2008) 381, 407-18.
Pelletier, et al. J. Biomol. Tech. (1998) acc. No. 50012
Remy & Michnick Proc. Natl. Acad. Sci. USA (1999) 96, 5394
Michnick. Curr. Opin. Struct. Biol. (2001) 11(4), 472-7
Michnick Nature Rev. (2007) 6, 569
Mossner et al. J. Mol. Biol. (2001) 308(2), 115-122

Secco et al. (2009) Prot. Evol. Des. Sel. 22(5), 149-158
Paulmurugan & Gambhir Anal. Chem. (2003) 75(7), 1584-9
Yao et al. Angew. Chem. Int. Ed. (2007) 46, 7031-4
Stefan et al. Proc. Natl. Acad. Sci. USA (2008) 104(43), 16916-21
Koch et al. J. Mol. Biol. (2006) 357, 427-441
Tawfik & Griffiths Nature Biotechnol. (1998) 16, 652-656
Dittrich et al. Chembiochem. (2005) 6(5):811-4
Baret et al. Lab Chip (2009) 9, 1850-1858
Ghadessy & Holliger Prot. Eng. Des. Sel. (2004) 17 (3), 201-4
Brouzes et al. PNAS (2009) Proc. Natl. Acad. Sci. USA 106(34), 14195-200

I claim:

1. A method for screening specific affinity molecules to target molecules using a homogeneous non-competitive assay, said method comprising: a) providing reagents of a homogeneous non-competitive assay, comprising: i) a target molecule, ii) a first molecule, and iii) a detection molecule that is a first member of a complementary pair, wherein the detection molecule is fused to the first molecule; b) combining a second molecule with said reagents of said homogeneous non-competitive assay, wherein said second molecule comprises a candidate affinity molecule fused to a complementary detection molecule that is a second member of the complementary pair, wherein the binding affinity of the candidate affinity molecule for the target is not known, and wherein said detection molecule and said complementary detection molecule generate a measurable signal upon binding of said candidate affinity molecules to said target; and c) identifying said candidate affinity molecule with affinity for said target as that generated a measurable signal in said homogeneous non-competitive assay.

2. A method of claim 1, wherein said affinity molecules are native antibodies, antibody fragments, artificial antibody scaffolds, peptides, or nucleic acids.

3. A method of claim 2, wherein said native antibodies are IgG, IgM, IgA, or IgE molecules.

4. A method of claim 2, wherein said antibody fragments include (Fab)$_2$, Fab, and scFv.

5. A method of claim 2, wherein said artificial antibody scaffolds include Nanobodies, Affibodies, Anticalins, DARPins, Monobodies, Avimers, and Microbodies.

6. A method of claim 2, wherein said peptides are greater than three amino acids, consist of either natural or non-natural amino acids, and include peptide aptamers.

7. A method in claim 6, wherein peptides are covalently attached to a carrier molecule.

8. A method of claim 2, wherein said nucleic acid includes nucleic acid aptamers and peptide nucleic acids (PNA).

9. A method of claim 2, wherein said molecules are expressed from genes or chemically synthesized.

10. A method of claim 2, wherein said affinity molecules comprise a tyrosine/serine binary-code interface.

11. A method of claim 2, wherein said affinity molecules comprise a tyrosine/serine/X amino acid tertiary-code interface.

12. A method of claim 1, wherein two or more affinity molecules are required to bind to at least 2 different epitopes of a target molecule.

13. A method of claim 1, wherein the first molecule is a reference affinity molecule and is known to bind the target with relatively high affinity, wherein the binding affinity of the candidate affinity molecule is not known, but is determined by the homogeneous assay.

14. A method of claim 13, wherein the reference affinity molecule has affinity for an epitope tag that is fused to the target.

15. A method of claim 14, wherein the epitope tag is polypeptide expressed along with the protein affinity molecule, including His-tag, FLAG-tag, V5-tag, Nano-tag, HA-tag, and c-myc-tag.

16. A method of claim 14, wherein the epitope tag is covalently bonded to the target.

17. A method in claim 13, wherein the candidate affinity molecule is derived from a library of potential affinity molecules.

18. A method in claim 13, wherein the binding of the reference affinity molecule and the candidate affinity molecule is an individual reaction.

19. A method in claim 13, wherein the binding reactions are performed in individual vessels.

20. A method in claim 13, wherein the individual vessels are reactions tubes.

* * * * *